United States Patent [19]

Sircar et al.

[11] Patent Number: 4,770,676
[45] Date of Patent: Sep. 13, 1988

[54] RECOVERY OF METHANE FROM LAND FILL GAS

[75] Inventors: Shivaji Sircar, Wescosville; Ravi Kumar, Allentown; William R. Koch, Fleetwood; John VanSloun, Allentown, all of Pa.

[73] Assignee: Air Products and Chemicals, Inc., Allentown, Pa.

[21] Appl. No.: 92,746

[22] Filed: Sep. 3, 1987

Related U.S. Application Data

[63] Continuation-in-part of Ser. No. 864,178, May 16, 1986, abandoned.

[51] Int. Cl.$^4$ .................................................. B01D 53/04
[52] U.S. Cl. ........................................... 55/26; 55/58; 55/62; 55/68
[58] Field of Search .................. 55/25, 26, 31, 33, 35, 55/58, 62, 68, 74, 75

[56] References Cited

U.S. PATENT DOCUMENTS

| | | | |
|---|---|---|---|
| 2,918,140 | 12/1959 | Brooks | 55/58 |
| 3,085,379 | 4/1963 | Kiyonaga et al. | 55/58 X |
| 3,176,444 | 4/1965 | Kiyonaga | 55/58 X |
| 3,594,983 | 7/1971 | Yearout | 55/33 |
| 3,751,878 | 8/1973 | Collins | 55/58 |
| 3,957,463 | 5/1976 | Drissel et al. | 55/58 X |
| 3,979,175 | 9/1976 | Kattan et al. | 55/58 X |
| 4,000,990 | 1/1977 | Bingham | 55/30 |
| 4,013,429 | 3/1977 | Sircar et al. | 55/33 |
| 4,077,779 | 3/1978 | Sircar et al. | 55/25 |
| 4,153,428 | 5/1979 | Saunders et al. | 55/26 |
| 4,249,915 | 2/1981 | Sircar et al. | 55/26 |
| 4,264,340 | 4/1981 | Sircar et al. | 55/25 |
| 4,314,828 | 2/1982 | Saito et al. | 55/26 |
| 4,329,158 | 5/1982 | Sircar | 55/26 |
| 4,409,102 | 10/1983 | Tanner | 210/603 |
| 4,472,178 | 9/1984 | Kumar et al. | 55/25 |
| 4,539,019 | 9/1985 | Koch | 55/58 X |
| 4,705,541 | 11/1987 | Sircar | 55/58 X |

OTHER PUBLICATIONS

Pressure Swing Adsorption for Natural Gas or Methane Recovery from Landfill Gas—E. Richter, K. D. Henning, K. Knoblauch and H. Juntgen, Bergbau-Forschung GmbH, Franz-Fischer-Weg 61, 43 Essen 13.
Literature Publication by Bergbau-Forschung "A New Process for the Production of High BTU Gas", W. R. Koch, 3/17/86.
Sales Brochure titled "Landfill Gas Treatment Experience with the GEMINI 5 System", K. F. Potochnik et al., 1987.
Sales Brochure titled "Landfill Gas Purification with the GEMINI 5 System", No. 522-604.

*Primary Examiner*—Robert Spitzer
*Attorney, Agent, or Firm*—Geoffrey L. Chase; William F. Marsh; James C. Simmons

[57] ABSTRACT

High purity methane and carbon dioxide are recovered from landfill gas in an integrated multi-column adsorption system having a temperature swing adsorption section (TSA) for pretreatment of the crude landfill gas to remove trace impurities therefrom, the thus cleaned gas being fed to a pressure swing adsorption section (PSA) for bulk separation of $CO_2$ from methane. Regeneration of the impurity-laden adsorbent bed of the TSA section is carried out using part of the $CO_2$ product gas recovered from the PSA section which gas is heated to thermal regeneration temperature.

38 Claims, 2 Drawing Sheets

RECOVERY OF METHANE FROM LAND FILL GAS

CROSS REFERENCE

The present invention is a continuation-in-part of U.S. application Ser. No. 864,178 filed May 16, 1986, now abandoned.

TECHNICAL FIELD OF INVENTION

The present invention is concerned with the purification and recovery of pure methane from landfill gas (LFG).

BACKGROUND OF THE INVENTION

Landfill gas contains a large number of trace hydrocarbon impurities and water which must be removed prior to the bulk separation of methane from carbon dioxide, which separation is generally carried out in a pressure swing adsorption (PSA) system. In order to obtain effective $CO_2/CH_4$ separation in the PSA system the water and hydrocarbon impurities need first to be removed from the crude LFG, since these impurities adversely effect the separation capacity of the selective adsorbent, such as zeolite, employed in the PSA system. If not removed the impurities end up in the product methane.

In a known previously utilized practice crude landfill gas was pretreated in a thermal swing adsorption (TSA) system to remove the water and hydrocarbon impurities prior to subjecting the LFG to separation of $CO_2/CH_4$ by PSA. The impurity-laden TSA adsorbent was regenerated, using part of the pretreated $CO_2$ and $CH_4$-containing stream or the eventual $CH_4$ product stream to heat the adsorbent. The same gas was used to cool the TSA adsorbent before a new cycle could be started. This procedure results in the loss of a significant amount of the cleaned feed gas ($CO_2+CH_4$) or of the valuable separated product gas ($CH_4$).

U.S. Pat. No. 4,000,990 discloses a landfill adsorptive separation process wherein a closed cycle regenerated pretreatment system is used in conjunction with a pressure swing adsorptive bulk separation of carbon dioxide and methane. The process of that patent suffers from the inefficiencies of closed loop regeneration of pretreatment beds wherein only gas contaminated by trace impurities is used to remove similar impurties from an offstream regenerating pretreatment bed. The result is that in that patent when a predetermined is brought back on-stream a certain level of residual impurities is carried over to the bulk separation pressure swing adsorption beds which are subsequently contaminated with impurities requiring periodic thermal regeneration resulting in disruption of the overall process and requiring large energy expenditures.

U.S. Pat. No. 4,329,158 discloses a process for separation of nitrogen from oxygen wherein a pretreatment adsorptive separation is performed prior to the bulk separation of the major constituents of air. Nitrogen enriched waste gas is utilized from the bulk separation portion of the process to regenerate the pretreatment portion of the process. The bulk separation of nitrogen from oxygen is performed with an elevated temperature adsorption of nitrogen, a desorption of bulk separation beds to a lower pressure, a purge of the beds with product oxygen after desorption countercurrently and two steps of repressurization to elevated pressure first with waste gas which is nitrogen enriched and secondly with product oxygen.

U.S. Pat. No. 4,077,779 discloses a process wherein methane and carbon dioxide can be resolved in a six step adsorptive pressure swing process including the steps of adsorption, high pressure rinse, depressurization, inert gas rinse, evacuation and repressurization.

In an article titled "Pressure Swing Adsorption for Natural Gas or Methane Recovery from Landfill Gas" hy E. Richter. et al., a process is disclosed which uses carbon molecular sieve or silica gel to separate carbon dioxide from methane in a biogas feed stream using pressure swing adsorption including the steps of pressure build-up adsorption expansion and evacuation.

In a literature publication by Bergbau-Forschung a process for methane recovery from a carbon dioxide-containing biogas stream is dismethane closed wherein pressure swing adsorption is used to perform the separation with a carbon molecular sieve. The steps include adsorption, depressurization. evacuation and pressure build-up.

In an article titled "A New Process for the Production of High BTU Gas" by W. R. Koch of Mar. 17, 1986, a process is disclosed wherein pretreatment of landfill off-gas is performed by adsorption followed by a bulk separation of methane from carbon dioxide and a pressure swing adsorption procedure including the steps of adsorption, high pressure rinse. depressurization, evacuation and repressurization. Details of pretreatment are not set forth.

In a sales brochure titled "Landfill Gas Treatment Experience With The GEMINI 5 System" by K. F. Potochnik, et al. of 1987, a process is set forth wherein landfill gas is treated in a pressure swing adsorption process including a pretreatment to remove minor contaminants and a bulk separation of carbon dioxide from methane using adsorption, high pressure rinse, depressurization, evacuation and repressurization. The pretreatment beds are recited to be regenerated with a regeneration gas which is thermally heated. Thereafter, the pretreatment bed is cooled down by a passage of a cool gas stream through the regenerated bed.

In yet another sales brochure titled "Landfill Gas Purification With The GEMINI 5 System" No. 522-604, a process for treating landfill gas is disclosed including the steps of feed compression and drying, a pretreatment stage which removes trace impurities for thermal combustion and venting followed by a pressure swing adsorption system which removes carbon dioxide for vent while retaining methane as a product stream for product compression.

Additional art of only general interest to the concept of adsorptive separation of gas mixtures include: U.S. Pat. Nos. 3,594,983; 3,751,878; 4,013,429; 4,249,915; 4,264,340; 4,314.828; 4,153.428; 4,472,178.

BRIEF SUMMARY OF THE INVENTION

In accordance with the present invention an integrated TSA-PSA process is employed wherein water and trace impurities present in the LFG are removed in the TSA pretreatment section prior to bulk separation of components in the cleaned gas to obtain essentially pure $CH_4$ and $CO_2$ respectively. In the integrated TSA-PSA process of the invention the TSA adsorbent beds are heated and cooled with a portion of the by-product $CO_2$ stream from the PSA section, which by-product stream is dry and free of impurities other than potentially minor amounts of methane. Thus, there is no sig-

DETAILED DESCRIPTION OF THE INVENTION

Figure 1:
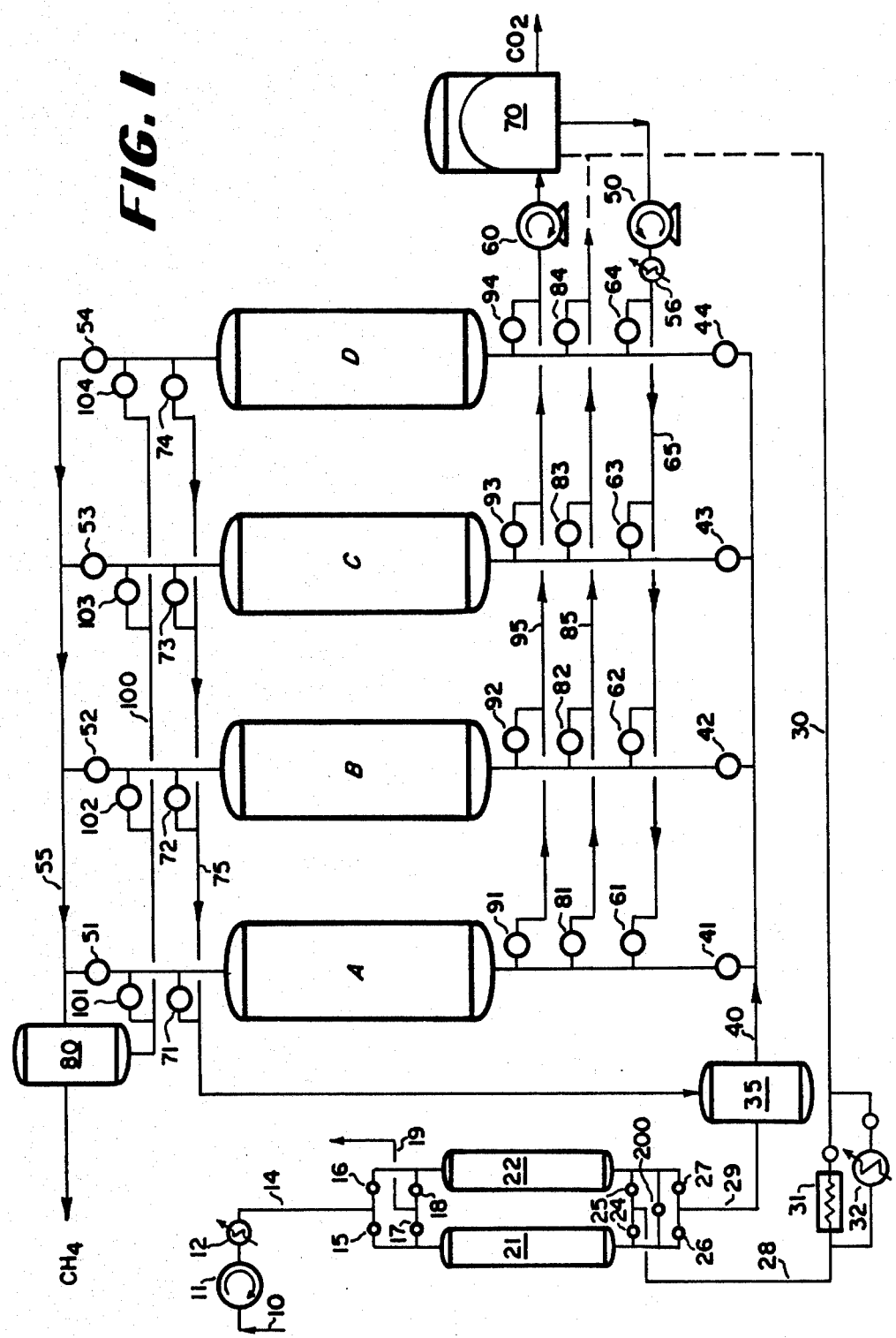
FIG. 1 is a schematic flow diagram illustrative of one embodiment of an integrated TSA/PSA system for practice of the invention.

As shown in FIG. 1, the TSA pretreat section comprises two adsorbent columns 21, 22 operated alternately in parallel such that during the period that one of these columns is on the adsorption stroke receiving impure LFG, the impurity-laden adsorbent bed in the companion column is being subjected to regeneration. In addition to the valving system required for the sequence of operational steps employed in the pretreat section, other essential and conventional pieces of equipment in the pretreat section include a gas feed compressor 11 and aftercooler/condenser 12. The impurity-freed gas discharged from the pretreatment section, comprised of about equal parts of $CH_4$ and $CO_2$, may be passed directly to one of the PSA columns, then on the adsorption stroke.

The PSA system illustrated comprises four adsorption Columns A, B, C, D, operated sequentially in parallel. In addition, the integrated system has among its major components a compressor 50 for $CO_2$, a vacuum pump 60, and a variable volume constant pressure or constant volume variable pressure storage vessel 70, in which part of the product gas is stored. The system further comprises vessels 35 and 80. Both of the vessels 35 and 80 are high pressure mixing vessels used as is hereinafter set out. The PSA section, as well as the TSA section are provided with the required switch valves and gas flow manifolds.

The TSA section, as such, is operated in conventional manner, the following sequence of steps being employed.

(a) Adsorption at super ambient pressure.
(b) Depressuring the adsorption column to ambient pressure level.
(c) Thermal regeneration of the adsorbent at elevated temperature in the column at ambient pressure.
(d) Cooling the regenerated adsorbent in the column.
(e) Repressuring the cooled column to the adsorption pressure.

The cycle time of step (a) is equal to the sum of the cycle times for steps (b) to (e), thus allowing continuous flow of cleaned feed to the PSA section. A total cycle time of 4 to 16 hours can be used in the TSA section.

The PSA section of the embodiment of FIG. 1 has the following cyclic step sequence:

(1) Selective adsorption of $CO_2$ at super ambient pressure while discharging unadsorbed $CH_4$.
(2) Co-current $CO_2$ rinse at near feed pressure with recycle of the effluent to the feed of another bed.
(3) Countercurrent depressurization of the column to near ambient pressure.
(4) Countercurrent evacuation of the column to subatmospheric pressure level.
(5) Countercurrent repressurization of the column to feed pressure using part of the clean $CH_4$ product.

Assuming that column 21 has been brought to the desired adsorption pressure (step e) for the start of a TSA cycle, it is charged with LFG feed while column 22 is undergoing the regeneration sequence. The land fill off-gas typically contains 30-70% methane mixed with 70-30% $CO_2$ besides a large number of saturated and unsaturated hydrocarbons, aromatic hydrocarbons, chlorinated hydrocarbons, etc. as impurities in trace levels (ppm), as well as water. Such gas is delivered to the TSA system by line 10, and compressed by feed compressor 11 to a selected pressure level in the range of 30-300 psig and then cooled to near ambient temperature in the cooler-condensor 12 where any resulting condensate is removed. The compressed gas is then passed by line 14 through one of the TSA columns, in this instance 21, which had then been previously regenerated, cooled and brought to feed pressure.

During the passage of the feed gas (step a) into and through column 21, valves 15 and 26 associated with that column are open while valves 17 and 24 are closed. Step (a) is continued for a predetermined time period during which the adsorbent in column 21 removes the trace impurities and water, at which time the flow of feed into column 21 is discontinued by closing valves 15 and 26, and feed introduction switched to column 22 by opening valves 16 and 27.

The LFG, freed of impurities in column 21, or in column 22 in turn, is discharged through line 29 into high pressure mixing vessel 35. Alternatively the purified gas in line 29 may be sent directly to the PSA section, entering the column then on the adsorption stroke (1).

Regeneration of the impurity-laden bed in column 21 is carried out (steps b to e) during the time that column 22 is on the adsorption stroke. Column 21 is depressured (b) to ambient pressure level by opening valve 17 thereby effecting discharge of gas from that column into line 19 which may be vented to the atmosphere, sent to a flare, or returned as feed to the suction of the compressor 11.

When column 21 is at ambient pressure level, heat is supplied to the bed of adsorbent therein to drive off sorbed impurities (c).

The hot gas used for regeneration is part of the pure $CO_2$ separated from the $CH_4$ in the PSA section of FIG. 1. The hot regeneration gas is supplied to the TSA section by line 28 through then opened valve 24 and discharged with desorbed products from column 21 into line 19 via open valve 17. At the end of the assigned heating period the bed in column 21 is cooled (d) by cold gas supplied through line 28 and passed through the bed via open valves 24 and 17 into discharge line 19.

At the termination of the cooling period, valve 17 is closed and column 21 is brought back to adsorption pressure by admission of compressed cleaned gas from companion column 22 or using part of the $CO_2$ product gas from the PSA section. In the latter modification the repressuring gas is admitted to column 21 via line 28 and open valve 24. If gas discharged from column 22 is to be used in repressuring column 21, valve 200 can be opened in a controlled fashion to connect vessels 21 and 22.

Table 1 below illustrates a time program for the TSA section employing a suggested four hour cycle, indicating valve positions during the cycle.

TABLE 1

| VALVE POSITIONS IN TSA SECTION | | | | | | | | | | |
|---|---|---|---|---|---|---|---|---|---|---|
| Column 21 | Column 22 | \multicolumn{9}{c}{Valve} |
| | | 15 | 16 | 17 | 18 | 24 | 25 | 26 | 27 | 200 |
| Ads. (a) | Depr. (b) | O | C | C | O | C | C | O | C | C |
| Ads. (a) | Heat (c) | O | C | C | O | C | O | O | C | C |
| Ads. (a) | Cool (d) | O | C | C | O | C | O | O | C | C |
| Ads. (a) | Repr. (e) | O | C | C | C | C | O/C | O | C | C/O |
| Depr. (b) | Ads. (a) | C | O | O | C | C | C | C | O | C |
| Heat (c) | Ads. (a) | C | O | O | C | O | C | C | O | C |
| Cool (d) | Ads. (a) | C | O | O | C | O | C | C | O | C |
| Repr. (e) | Ads. (a) | C | O | C | C | O/C | C | C | O | C/O |

O = Open
C = Closed
Ads. = Adsorption
Depr. = Depressurize
Heat = Thermal regeneration
Cool = Cooling bed
Repr. = Repressurizing During a four hour total cycle, each of the TSA columns alternately will be on the adsorption stroke for half that period (2 hours), then on steps (b) to (e) for two hours. Each of the steps (b) to (e) may be designed for equal 30 minute periods, or if preferred the two hours may be divided, assigning longer time periods for the heating and cooling steps (c) and (d) than that used in steps (b) and (e).

The hot gas employed in regeneration of the adsorbent beds of the TSA section is supplied by an effluent from the PSA section as hereinafter described. Such regeneration gas is passed by line 30 through a heater 31 into line 28, discharging into column 21 or 22 then on the thermal regeneration step (c), through open valve 24 or 25 respectively. At the termination of the heating step gas from line 30 is switched to flow through a cooler 32 before entering line 28, feeding the cooling gas to the column (21 or 22) then on step (d). The cooler may be eliminated if the column is cooled down to only ambient temperature. In that case cooling can be achieved by switching off the heater 31. The thermal regeneration may be carried out using gas heated to 250° to 900° F. In the subsequent cooling step the cooled gas is supplied to the column then on step (d) at a temperature in the range of 40° to 120° F., to restore the column to a subambient or ambient temperature level.

The clean gas discharged from the TSA section of FIG. 1 through line 29 is passed into the high pressure mixing vessel 35 from which it is withdrawn by line 40 and charged into one of the columns of the PSA section of FIG. 1 then on the adsorption stroke. Assuming that column A is on the adsorption stroke, having been previously brought to designed adsorption pressure, the feed gas comprised essentially of $CO_2$ and $CH_4$, is introduced into column A through then opened valve 41. The feed gas passes through the bed of adsorbent in column A whereby the $CO_2$ is selectively adsorbed and an effluent stream of substantially pure methane is discharged through open valve 51, into gas discharge manifold 55. During the adsorption stroke (1) only valves 41 and 51 associated with column A are open. Adsorption is continued until the $CO_2$ level approaches the accepted level in the high purity $CH_4$ effluent.

At the termination of the adsorption stroke valves 41 and 51 are closed and feed gas flow is switched into one of the other columns of the PSA section of FIG. 1. The adsorbent in column A being saturated with sorbed $CO_2$, is now rinsed at the prevailing super-atmospheric pressure with a stream of high purity $CO_2$. The rinse stream is obtained from the storage vessel 70. Stored $CO_2$ is withdrawn from vessel 70 and compressed by compressor 50 to slightly above feed pressure level and cooled by cooling means 56 to near ambient temperature. The cooled $CO_2$ stream is passed into column A (step 2) through supply manifold 65, discharging into column A through open valve 61. The $CO_2$ rinse gas passes through column A in a direction co-current to that of the previous feed gas and is discharged from column A via open valve 71 into manifold 75.

The effluent from column A during the rinsing step (2) has a composition similar to that of the feed gas. It is mixed in a mixing vessel 35 with fresh purified feed gas from the TSA section and the mixture employed as feed to the PSA section adsorber columns. The rinsing step is continued until the column undergoing that step (2) is essentially saturated with pure $CO_2$.

At the termination of the rinsing of column A, valves 61 and 71 are closed and valve 81 is opened to depressure that column to near-ambient pressure level (step 3) in a direction counter to that of the feed. At the reduced pressure the sorbed high purity $CO_2$ flows out of column A into discharge manifold 85. The gas in manifold 85 may be wholly or partly stored in vessel 70 (as indicated by the dashed line leading to that vessel) or it may be partly rejected. The gas, whether from vessel 70 or directly from line 85, may be used for regeneration of the TSA section as hereinbefore indicated. Since this gas is comprised of high purity $CO_2$ the non-used part may be collected in vessel 70 or withdrawn separately therefrom as a useful product for use or sale.

When column A is near the ambient pressure level valve 81 is closed and valve 91 is opened to initiate the evacuation step (4). Through open valve 91 the residual gas content (high purity $CO_2$) is withdrawn from column A by vacuum pump 60 via line 95 and may be passed into storage vessel 70. By using the vacuum pump 60 the column pressure is brought down to about 50-300 torr level by gas withdrawal in a direction counter to that of the feed. The part of the high purity $CO_2$ withdrawn by evacuation and not used in regeneration of the TSA section may be collected as useful product gas.

When desired evacuation has been completed, valve 91 is closed and valve 101 is opened for initiation of the repressuring step (5). The repressuring is effected by withdrawing part of the high purity $CH_4$ from vessel 80 via line 100 and flowing the same through open valve 101 into column A in a direction counter to feed until that column is brought back to approximately the feed pressure level. At the conclusion of the repressuring step (5) the described cycle of operations is repeated in the described sequence. Each of the PSA columns of FIG. 1 in turn undergoes the same sequence of steps as that described in connection with column A. Table 2 illustrates a time program for the various steps in the sequence of operations of the PSA section based on an embodiment employing a suggested 12 minute cycle and indicating the valve positions during the sequence. It will be understood, however, that the 12 minute cycle described is merely illustrative and that other time cycles may be employed in practice of the invention, with or without change in the number of adsorption columns utilized in the PSA section.

TABLE 2

| COL | 0 to 1.5 | 1.5 to 3.0 | 3.0 to 4.5 | 4.5 to 6.0 | 6.0 to 7.5 | 7.5 to 9.0 | 9.0 to 10.5 | 10.5 to 12.0 | | 0 to 1.5 | 1.5 to 3.0 | 3.0 to 4.5 | 4.5 to 6.0 | 6.0 to 7.5 | 7.5 to 9.0 | 9.0 to 10.5 | 10.5 to 12.0 |
|---|---|---|---|---|---|---|---|---|---|---|---|---|---|---|---|---|---|
| A | Ad | Ad | R | R | Dp | E | E | Pr | | Ad | Ad | R | R | Dp | E | E | Pr |
| B | E | Pr | Ad | Ad | R | R | Dp | E | | E | Pr | Ad | Ad | R | R | Dp | E |
| C | Dp | E | E | Pr | Ad | Ad | R | R | | Dp | E | E | Pr | Ad | Ad | R | R |
| D | R | R | Dp | E | E | Pr | Ad | Ad | | R | R | Dp | E | E | Pr | Ad | Ad |
| | | | | | | | | VALVE POSITION | | | | | | | | | |
| 41 | O | O | C | C | C | C | C | C | 81 | C | C | C | C | O | C | C | C |
| 42 | C | C | O | O | C | C | C | C | 82 | C | C | C | C | C | C | O | C |
| 43 | C | C | C | C | O | O | C | C | 83 | O | C | C | C | C | C | C | C |
| 44 | C | C | C | C | C | C | O | O | 84 | C | C | O | C | C | C | C | C |
| 51 | O | O | C | C | C | C | C | C | 91 | C | C | C | C | C | O | O | C |
| 52 | C | C | O | O | C | C | C | C | 92 | O | C | C | C | C | C | C | O |
| 53 | C | C | C | C | O | O | C | C | 93 | C | O | O | C | C | C | C | C |
| 54 | C | C | C | C | C | C | O | O | 94 | C | C | C | O | O | C | C | C |
| 61 | C | C | O | O | C | C | C | C | 101 | C | C | C | C | C | C | C | O |
| 62 | C | C | C | C | O | O | C | C | 102 | C | O | C | C | C | C | C | C |
| 63 | C | C | C | C | C | C | O | O | 103 | C | C | C | O | C | C | C | C |
| 64 | O | O | C | C | C | C | C | C | 104 | C | C | C | C | C | O | C | C |
| 71 | C | C | O | O | C | C | C | C | | | | | | | | | |
| 72 | C | C | C | C | O | O | C | C | | | | | | | | | |
| 73 | C | C | C | C | C | C | O | O | | | | | | | | | |
| 74 | O | O | C | C | C | C | C | C | | | | | | | | | |

O = Open
C = Closed
Ad: Adsorption
R: $CO_2$ Rinse
Dp: Depressuring
E: Evacuation
Pr: Pressuring The adsorbent(s) employed in the pretreat section is one selective in retaining impurities present in feed gas, which includes trace hydrocarbons heavier than methane, chlorinated hydrocarbons, etc., as well as residual water vapor. An example of the trace impurities is given in the following Table 3.

TABLE 3

| Raw LFG Impurities | |
|---|---|
| Compound | Conc. (ppm) |
| Pentane | 5 |
| 1,1 dichloroethylene | 1 |
| dichloromethane | 12 |
| 1,2 dichloroethane | 4 |
| 1,1 dichloroethane | 8 |
| Hexane | 28 |
| Benzene | 23 |
| Iso-octane | 4 |
| Trichloroethane | 8 |
| Toluene | 210 |
| Tetrachloroethylene | 35 |
| 1,1,2 trichloroethylene | 0.1 |
| Chlorobenzene | 11 |
| Ethylbenzene | 54 |
| Xylenes | 116 |
| Nonane | 12 |
| Isopropyl benzene | 28 |
| Propyl benzene | 4 |
| Napthalene | 0.1 |

Typical adsorbent preferred for this purpose is activated carbon with which a water retaining adsorbent is admixed or provided as a separate layer in the TSA column. The water-retaining adsorbent component may be activated carbon, alumina, silica gel or an alumniosilicate molecular sieve zeolite.

For the separation of $CO_2/CH_4$ in the PSA section it is preferred to employ 13X zeolite as the $CO_2$-retaining adsorbent. Other adsorbents that may be employed in the PSA section include zeolites such as 5A, Silicalite, mordenite or activated carbon in lieu of the 13X zeolite or in combination therewith. The zeolites (A, X, mordenite) can be ion exchanged with single ions from groups I and II metals or binary exchanged with two metals from these groups.

EXAMPLE 1

The performance of the PSA section was evaluated in a bench scale unit after pretreatment to remove water and trace contaminants from the feed gas in a thermal swing adsorber consisting of 4.5 lbs. of an activated carbon and 1.5 lbs. of 13X zeolite. The impurities in the feed gas were those listed in Table 1. The pretreatment column was regenerated at about 850° F. The feed gas to the pretreatment column contained 42.5% $CO_2$ and 57.5% $CH_4$ and the pressure was 70 psig. An adsorption time of 4 hours was used. The pretreated feed was fed at 70 psig and 21° C. into a column containing 7 pounds of 13X zeolite. The unadsorbed effluent withdrawn from the column at 69 psig contained 99% $CH_4$. During the adsorption step 0.013 pound moles of feed gas was passed through the column. After termination of the adsorption step the column was rinsed with $CO_2$ of 99% purity at 72 psig and the rinse effluent was recycled as feed to the adsorption step. Following $CO_2$ rinsing the column was depressured to ambient pressure level and then evacuated to 95 torr. The obtained effluent comprised 98.5% $CO_2$, part of which was withdrawn as $CO_2$ product and the other part was recompressed as recycled $CO_2$ rinse. Following evacuation the column was repressured to 70 psig using part of the 99% pure $CH_4$ product and the cycle repeated.

The amounts of $CO_2$ products recovered from the system were 0.0074 pound moles $CH_4$ and 0.0056 pound moles of $CO_2$, each at 99% purity. Thus, the product recovery of both constituents of the feed mixture were 99% (within experimental error).

While the PSA system described and illustrated in FIG. 1 employed a four adsorbent column configuration a five column configuration can be used to eliminate storage tank 80, or both storage tanks 70 and 80 can be eliminated by using a six adsorbent column configuration in the PSA section. Alternately a two or three adsorbent column system can be designed to accommodate the cycle described above by allowing the vacuum pump or the compressor to idle for parts of the cycle.

Figure 2:
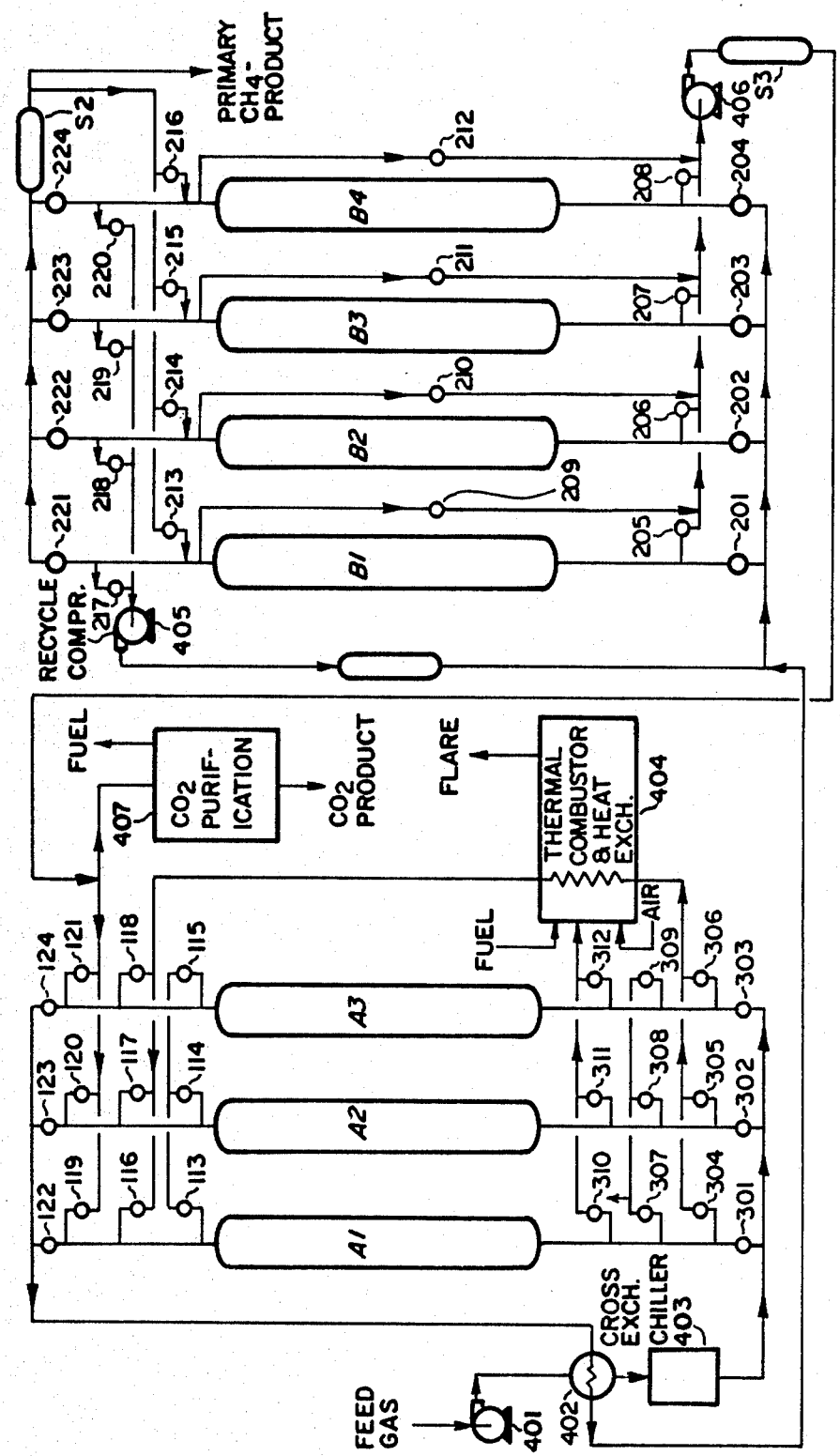
FIG. 2 is a schematic flow diagram illustrative of another embodiment of an integrated TSA/PSA system for the practice of the invention.

A second embodiment of the present invention is directed to a landfill gas resolution using two or three beds of pretreatment to remove impurities followed by a bulk separation of methane as a primary product and carbon dioxide containing minor amounts of methane as a by-product in a four step process comprising adsorption, depressurization, evacuation and repressurization of each of the beds of the bulk separation. This bulk separation eliminates the high pressure rinse after adsorption as used in the first embodiment described above of the present invention. The difference in the sequence of steps in the respective embodiments of the bulk separation results in the non-rinse embodiment retaining a minor methane content ($\sim 3.6\%$) in the carbon dioxide by-product versus the insignificant methane content ($\sim 1.0\%$) in the carbon dioxide product in the initial embodiment involving five steps of bulk separation processing. The methane content in the carbon dioxide by-product of the bulk separation of this second embodiment utilizing four steps without a high pressure rinse can be tolerated when the methane-containing carbon dioxide by-product is used for regeneration of the pretreatment beds and the regeneration gas is subsequently delivered to a thermal combuster for destruction of the pretreatment contaminants whereby the methane content constitutes at least a portion of the fuel value necessary to effect the thermal combustion of the impurities evolved from the regeneration of the pretreatment beds. A description of the second embodiment which is illustrated in FIG. 2 will now be set forth in general terms and then with specific reference to the illustration in FIG. 2. Although this embodiment can be run in either a two or three bed pretreatment mode, only the three bed mode will be described because the two bed mode has already been described with reference to the first embodiment of the present invention illustrated in FIG. 1.

The main difference in the two options is during the carbon dioxide regeneration steps. For the three bed process, cold and hot purge steps are carried out simultaneously by the same $CO_2$ stream as compared with the two bed process in which cold and hot purge steps are carried out sequentially, thereby increasing the regeneration gas requirement. Typical process cycles for both the options are listed in Table 4. Eight hour adsorption cycle time is chosen as an example.

TABLE 4

Process Steps - TSA Front End Clean Up

A. Two Bed Cycle -

| Time (Minutes) | Column A1 | Column A2 |
|---|---|---|
| 0–20 | Adsorption | Depressurization |
| 20–240 | Adsorption | Hot Purge |
| 240–460 | Adsorption | Purge |
| 460–480 | Adsorption | Pressurization |
| 480–500 | Depressurization | Adsorption |
| 500–720 | Hot Purge | Adsorption |
| 720–940 | Purge | Adsorption |
| 940–960 | Pressurization | Adsorption |

B. Three Bed Cycle -

| Time (Minutes) | Column A1 | Column A2 | Column A3 |
|---|---|---|---|
| 0–20 | Adsorption | — | De-pressurization |
| 20–460 | Adsorption | Purge | Hot Purge |
| 460–480 | Adsorption | Pressurization | — |
| 480–500 | Depressurization | Adsorption | — |
| 500–940 | Hot Purge | Adsorption | Cold Purge |
| 940–960 | — | Adsorption | Pressurization |
| 960–980 | — | Depressurization | Adsorption |
| 980–1420 | Cold Purge | Hot Purge | Adsorption |
| 1420–1440 | Pressurization | — | Adsorption |

Process steps for the three bed option will now be described.

The Adsorption Step consists of flowing the landfill gas, which is saturated with water and contains bulk methane (30–70%), carbon dioxide (70–30%), and other trace contaminants at P $\sim 30$–300 psia and T $\sim 40°$–150° F., through a column packed with adsorbent or adsorbents capable of selectively removing water, hydrogen sulfide and other trace impurities from the feed gas and withdrawing an effluent stream which now essentially contains bulk methane and carbon dioxide. This stream is fed to the $CO_2/CH_4$-PSA bulk separation system. These steps are continued for a predetermined cycle time or, until the concentration of a key trace component in the effluent stream or inside the adsorption column has reached a preset limit. The column is now called "spent" because it has exhausted its capacity for removing the trace contaminants.

Next, a Depressurization Step is performed which consists of discontinuing the feed flow through the "spent" column and transferring the feed to another front end TSA pretreatment column while reducing the pressure in the spent column to $\sim 15$ psia by venting the gas in direction opposite to the feed flow.

This is followed by a Hot Purge Step, which consists of flowing carbon dioxide purge gas, which is essentially free of trace impurities and may contain up to 6% methane at P $\sim 15$ psia and is heated to T $\sim 250°$–900° F. in direction opposite to the feed flow. This purge gas is obtained as effluent from a pretreatment column on cold purge regeneration (described below), and is heated to the regeneration temperature by flowing through a thermal combustor. The resulting hot effluent is withdrawn from the column, and the hot effluent essentially contains all the trace impurities at much higher concentration levels. It is mixed with external fuel and air to burn it in the thermal combustor. This step thermally destroys all the trace impurities and generates energy for heating the regeneration gas to regenerate other columns of the three column pretreatment zone. The hot purge is continued for a preset cycle time or until the temperature of the effluent gas reaches a preset limit. The flow of hot gas is then discontinued.

Then a Cold Purge Step is performed, which consists of flowing carbon dioxide purge gas, which is essentially free of trace impurities and may contain up to 6% methane at P $\sim 15$ psia in direction opposite to the feed flow. This purge gas is obtained as the evacuated gas from the $CO_2/CH_4$-PSA bulk separation system. This effluent is withdrawn from the adsorption column and flows through the thermal combustor for heating. This gas is then used for the hot purge step above. The cold purge step is continued for a preset cycle time or until the temperature of the effluent gas reaches a preset limit. The flow of cold gas is then discontinued. The column is now called "regenerated."

Finally, a Pressurization Step is performed, which consists of connecting the regenerated column with an adsorbing pretreatment column which is now undergoing the adsorption step, and pressurizing the regenerated column with trace impurity-free effluent from the other column from P15 psia to adsorption pressure ~30–300 psia. The direction of flow into the regenerated column during pressurization is opposite to the direction of feed flow during adsorption step. This is continued until the pressure in the regenerated column has reached the adsorption pressure. This pretreatment column is now ready to undergo a new cycle starting from the adsorption step.

The bulk separation pressure swing adsorption separation of landfill gas ($CO_2/CH_4$) will now be described ($CO_2/CH_4$-PSA). Trace contaminant free landfill gas, containing primarily carbon dioxide and methane is fed to the PSA bulk separation section for separating $CO_2$ and $CH_4$. Before entering a column on an adsorption step, the effluent from the pretreatment TSA section is mixed with gas from the depressurization step of the bulk separation PSA section described below.

The Adsorption Step consists of flowing the trace impurity-free landfill gas at P ~30–300 psia and T ~40°–150° F., through a column packed with an adsorbent capable of selectively removing carbon dioxide from the feed gas and withdrawing an effluent stream which now is essentially high purity methane from the bulk separation column on the adsorption step. This step is continued for a predetermined cycle time or, until the concentration of carbon dioxide in the effluent stream reaches a preset limit. The column is now called "spent" because it has exhausted its capacity for removing carbon dioxide.

Next a Depressurization Step is performed, which consists of one of two options. The first option is to discontinue the feed flow through the "spent" column and to transfer the feed to another PSA column, reduce the pressure in the spent column to ~15 psia by venting the gas in a direction either opposite to or same as the feed flow, and raise the pressure of all the depressurized gas to the same level as the feed gas pressure in the adsorption step by a compressor, followed by mixing the compressed gas with the feed gas and feeding the mixed gas to the bulk separation column on adsorption. The second option is to discontinue the feed flow through the "spent" column and transfer the feed to another bulk separation PSA column, then reduce the pressure in the spent column to a middle pressure level of 20–160 psia by joining it with the feed end of a column which is being repressurized from an evacuated condition of the bulk separation PSA cycle. The gas flow direction in the depressuring column is either opposite to or same as the feed flow in adsorption. The depressurizing column is further reduced in pressure to ~15 psia by venting the gas in a direction either opposite to or same as the feed flow. Then the pressure of all the vented gas in the above step is raised to the same level as the feed gas pressure in the adsorption step by a compressor. The gas from the above step is then mixed with the feed gas and the resulting mixed gas is fed to the bulk separation PSA column on an adsorption step. Thereafter an Evacuation Step is performed, which consists of two options also. In the first option, further lowering the pressure of the depressurized column from P ~15 psia to P ~50–300 torr, by evacuating the gas from the feed end of the column is performed, while storing the evacuated gas, which is essentially trace impurity-free carbon dioxide for further use. In the second option, further lowering the pressure of the depressurized column from P ~15 psia to P ~50–300 torr, by simultaneously evacuating the gas from both the feed and the product ends of the column is performed, while storing the evacuated gas, which is essentially trace impurity-free carbon dioxide for further use.

Finally, a Repressurization Step is performed, which consists of discontinuing the pressure reduction of the column. The column is now called "regenerated" because its capacity for carbon dioxide removal has been restored. Then, one of two options can be performed. The first option involves raising the pressure in the regenerated column from evacuation level (50–300 torr) to adsorption level (30–300 psia) by connecting the product end of the regenerated column with product end of the column on the adsorption step and then discontinuing the above step when pressure in the regenerated column has reached the desired level. The second option involves raising the pressure in the regenerated column from evacuation level (50–300 torr) to some middle level by connecting the feed end of the regenerated column with the depressurizing end of the column on the depressurization sequence where the second option middle level depressurization is performed. The pressure in the regenerated column is raised from middle level to adsorption level (30–300 psia) by connecting the product end of the regenerated column with the product end of the column on adsorption. The above step is discontinued when the pressure in the regenerated column has reached the desired level.

This column is now ready to undergo a new cycle starting with the adsorption step.

The above PSA cycle needs at least two trains of adsorption columns for continuous feed and product flow. Three or four trains may be used for continuous operation of the other pieces of the rotating machinery. Some of the possible options with a typical adsorption time of five minutes are listed in Table 5. Flow schematic of one of the options is given in FIG. 2.

TABLE 5

Process Steps - PSA $CO_2/CH_4$ Separation

A. Two Bed Cycle -

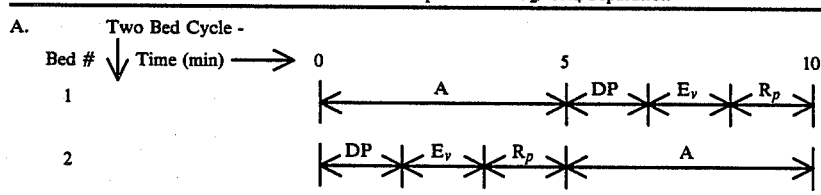

TABLE 5-continued

Process Steps - PSA CO$_2$/CH$_4$ Separation

B. Three Bed Cycle -

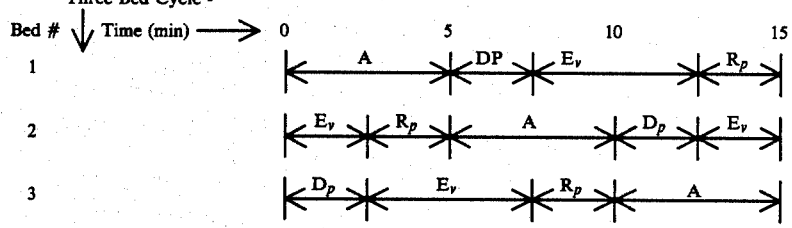

C. Four Bed Cycles -

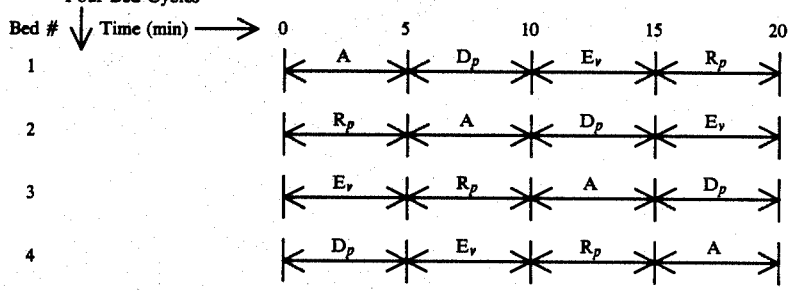

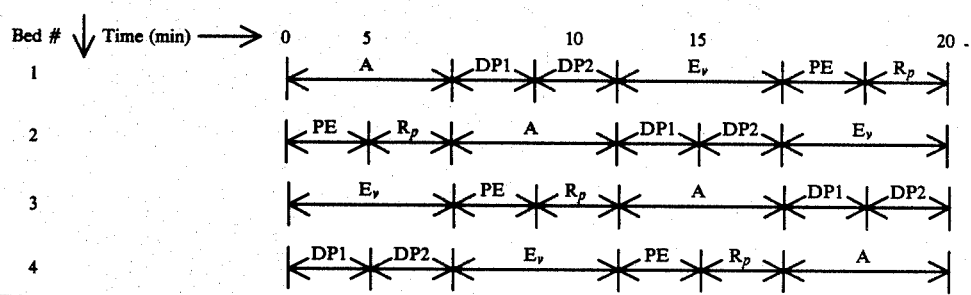

A — Adsorption Step
DP — Depressurization from adsorption pressure to ambient pressure.
DP1 — First depressurization from adsorption pressure to some middle pressure level, coupled with PE.
DP2 — Final depressurization from middle pressure level to ambient pressure.
E$_v$ — Evacuation from ambient pressure to sub-atmospheric pressure level.
PE — Pressure increase from sub-atmospheric level to some middle level by pressure equalization with a column on DP1.
R$_p$ — Repressurization by product methane up to adsorption level.

Any methane-containing carbon dioxide which is not used for pretreatment regeneration can be purified and recovered as a product. Any process such as liquifaction, capable of producing commercial grade carbon dioxide, may be used. The by-product methane from the process is used in part or its entirety as fuel for the TSA-thermal combustor. The remaining methane, not used in the thermal combustor is mixed with the methane product.

A detailed process description of the schematic for the second embodiment of the process is given for FIG. 2. Typical process steps for the frontend-TSA and CO$_2$/CH$_4$-PSA are given in Tables 4 and 5. The valve positions for the three column option of the TSA system are given in Table 6, and for one of the four bed PSA options are given in Table 7. Process description at typical operating conditions is given below.

For the TSA pretreatment columns, landfill gas compressed to $P \sim 100$ psia and $T \sim 70°-150°$ F., by the feed gas compressor 401 enters the cross heat exchanger 402 and is heat exchanged against the TSA product stream. The heat exchanged feed stream is further cooled by the chiller 403 to $T \sim 40°-70°$ F. before entering one of the adsorption columns, let us say A1 via open valve 301. Column A1 has been previously pressurized to the adsorption pressure, $P \sim 100$ psia. Column A1 is in communication with CO$_2$/CH$_4$ PSA system via open valve 122. The effluent gas from A1 is cross exchanged against the feed stream in heat exchanger 402. Feed to Column A1 is continued for a predetermined cycle time or until the concentration of a key impurity reaches a predetermined level in the effluent stream, or at a certain location inside the adsorption column. The feed is now switched to Column A2 via open valve 302. Column A1 is depressurized to $\sim 15$ psia via open valve 307. Column A1 is then purged with trace impurity-free carbon dioxide obtained as effluent from Column A3 and heated to $T \sim 250°-900°$ F. by heat exchanging it in the thermal combustor 404 and entering Column A1 via open valve 116. The effluent from Column A1 enters thermal combustor 404 via open valve 310 where it is burnt and all the impurities are destroyed. The hot purge gas flow to Column A1 is stopped and cold purge gas flow is started. after a preset time or temperature level of the effluent gas stream. via open valve 119. The trace impurity-free carbon dioxide for the cold purge step is obtained as the secondary product from the CO$_2$/CH$_4$ - PSA system. The cold purge gas exits Column A1 via open valve 304 and enters the thermal combustor 404 to be heated to $T \sim 300°-600°$ F. and is used as the hot purge gas for Column A2. The purge gas flow is discontinued after a preset time or temperature limit. Column A1 is now connected with Column A3 undergoing the feed step, via open valves 113 and 115, and pressurized from P ~15 psia to P ~100 psia by trace impurity-free effluent from Column A3. Column A1 is now ready to go on-stream. Valve position are shown in Table 6.

TABLE 6

Valve Sequence - Pretreatment TSA (FIG. 2)

| Time (Minutes) | 301 | 302 | 303 | 304 | 305 | 306 | 307 | 308 | 309 | 310 | 311 | 312 |
|---|---|---|---|---|---|---|---|---|---|---|---|---|
| 0-20 | O | | | | | | | | O | | | |
| 20-460 | O | | | O | | | | | | | | O |
| 460-480 | O | | | | | | | | | | | |
| 480-500 | | O | | | | | O | | | | | |
| 500-940 | | O | | | | O | | | | O | | |
| 940-960 | | O | | | | | | | | | | |
| 960-980 | | | O | | | | | O | | | | |
| 980-1420 | | | O | O | | | | | | | | |
| 1420-1440 | | | O | | | | | | | | | |

| Time (Minutes) | 113 | 114 | 115 | 116 | 117 | 118 | 119 | 120 | 121 | 122 | 123 | 124 |
|---|---|---|---|---|---|---|---|---|---|---|---|---|
| 0-20 | | | | | | | | | | O | | |
| 20-460 | | | | | | O | | O | | O | | |
| 460-480 | O | O | | | | | | | | O | | |
| 480-500 | | | | | | | | | | | O | |
| 500-940 | | | | O | | | | | O | | O | |
| 940-960 | | O | O | | | | | | | | O | |
| 960-980 | | | | | | | | | | | | O |
| 980-1420 | | | | O | | O | | | | | | O |
| 1420-1440 | O | O | | | | | | | | | | O |

O — Valve open, otherwise closed.

For the bulk separation of $CO_2$ and $CH_4$ in the PSA, trace impurity-free mixture of carbon dioxide and methane enters one of the $CO_2/CH_4$ - PSA section columns, let us say B1 at P ~100 psia and T ~100° F. via open valve 201. Column B1 has been previously pressurized to the adsorption pressure, P ~100 psia. Effluent from Column B1, primarily methane product enters the storage vessel $S_2$ via open valve 221. From storage vessel $S_2$ methane product is withdrawn continuously while part of it is used for repressurizing another PSA column. The feed step is continued for a predetermined time or till carbon dioxide concentration in the effluent stream reaches a preset limit. At which time the feed is switched to another adsorption Column B2, via open valve 202. Pressure in Column B1 is now reduced to P ~15 psia via open valve 217. The depressurized gas is compressed to the feed pressure P ~100 psia by the recycle compressor 405 and is mixed with the effluent from TSA section and is fed to the column on adsorption step at this time, Column B2. Alternatively, depressurization gas could be recovered as a $CO_2$ product.

Pressure in Column B1 is further reduced from P ~15 psia to P ~40-200 torr, via open valves 205 and 209 and vacuum pump 406. The evacuated gas is stored in storage tank S3. This constitutes the secondary product—$CO_2$. Part of this gas is used for regenerating the front end TSA section while the remainder is further purified by $CO_2$ purification system - 407. Alternatively, depressurization gas could be used to regenerate the TSA section by itself or in combination with evacuation gas. The evacuation step is discontinued after a predetermined time or when the pressure in Column B1 has reached a preset level. Column B1 is now connected with storage vessel $S_2$ via open valve 213 and pressurized to the adsorption pressure, P ~ 100 psia. Column B1 is now ready to go on-stream. Valve positions are shown in Table 7.

TABLE 7

Valve Sequence - Bulk Separation $CO_2/CH_4$ PSA (FIG. 2)

| Time (Minutes) | 201 | 202 | 203 | 204 | 205 | 206 | 207 | 208 | 209 | 210 | 211 | 212 |
|---|---|---|---|---|---|---|---|---|---|---|---|---|
| 0-5 | O | | | | | | O | | | | O | |
| 5-10 | | O | | | | | | O | | | | O |
| 10-15 | | | O | | O | | | | | O | | |
| 15-20 | | | | O | | O | | | | | O | |

| Time (Minutes) | 213 | 214 | 215 | 216 | 217 | 218 | 219 | 220 | 221 | 222 | 223 | 224 |
|---|---|---|---|---|---|---|---|---|---|---|---|---|
| 0-5 | | O | | | | | | O | O | | | |
| 5-10 | | | O | O | | | | | | O | | |
| 10-15 | | | | | O | O | | | | | O | |
| 15-20 | O | | | | | | O | | | | | O |

O — Valve Open, otherwise closed.

EXAMPLE 2

Table 8 lists a typical example for obtaining trace impurity-free methane and carbon dioxide from landfill gas using the second embodiment of the present invention. Overall methane recovery from the suggested system is ~97.7% and carbon dioxide recovery is ~55.6% the balance of the carbon dioxide is used as regeneration gas. Typical operating conditions and plant size are also listed in Table 8. TSA columns are packed with adsorbents having an affinity for the particular impurities in the feed. The PSA columns are packed with a carbon dioxide selective zeolite.

TABLE 8

An Example of the Suggested Cycle

|  | Feed | Product Methane | Product Carbon Dioxide |
|---|---|---|---|
| P(atm) | 7 | 7 | 1 |
| T(°F.) | 70 | 70 | 70 |
| Flow Rate (lbmole/hr) | 657.3 | 371.4 | 163 |
| Composition: |  |  |  |
| CH$_4$(%) | 57 | 98.6 | 3.6 |
| CO$_2$(%) | 43 | 1.4 | 96.4 |
| Trace Impurities | Table 1 | N.D. | N.D. |
| Water | Saturated | N.D. | N.D. |

N.D.—Non-dectectable

The second embodiment of the present invention produces trace impurity-free methane and carbon dioxide by efficiently and effectively integrating the CO$_2$/CH$_4$ - PSA system with front end TSA and CO$_2$ purification cycles. There are several differences as compared with the first embodiment described earlier, first of which is the PSA cycle for CO$_2$/CH$_4$ separation.

The first embodiment of the present invention employs a high pressure CO$_2$ rinse step. The advantage of this step is to increase the methane recovery of the PSA cycle to ~98.9% and CO$_2$ purity of the evacuated gas to —98.6%. However since part or all of the evacuated gas is used for regenerating the front end TSA system, the regeneration gas has to be supplemented by additional fuel gas from the pretreatment system. This results in overall methane recovery of —97.8% from the first embodiment of the present invention.

The second embodiment of the present invention does not employ a high pressure CO$_2$ rinse step. Instead, the depressurized gas is directly compressed and mixed with the feed gas to increase methane recovery. The only methane loss from the PSA system occurs in the evacuated gas. However, in the second embodiment of the present invention this loss is controlled by selecting the right adsorbent. Methane concentration in the evacuated gas is a strong function of CO$_2$-CH$_4$ selectivity, where the selectivity is defined as:

$$S = \frac{CO_2 \text{ - Solid Phase Capacity}}{CO_2 \text{ - Gas Phase Mole Fraction}} \cdot \frac{CH_4 \text{ - Gas Phase Mole Fraction}}{CH_4 \text{ - Solid Phase Capacity}}$$

Any adsorbent with S higher than ~15 and preferably higher than ~20 gives methane concentration less than ~6% in the evacuated gas. 6% is the maximum amount of methane needed in the evacuated gas so that no external fuel is required for regenerating the front end TSA system. By operating the second embodiment of the present invention in this manner overall methane recovery of ~97.7% is obtained, which is essentially the same as the methane recovery from the first embodiment of the present invention.

As compared with U.S. Pat. No. 4,000,990, higher methane recovery is observed by compressing *all* the depressurized gas and choosing the adsorbent so as not to loose methane in evacuated gas. In addition. the methane and carbon dioxide from the second embodiment process are trace impurity-free, which is not the case with U.S. Pat. No. 4,000,990.

The thermal swing adsorption system in U.S. Pat. No. 4,000,990 regenerates the spent adsorbent by recirculating the same gas in the regeneration loop. This results in product methane and carbon dioxide streams containing trace impurities. This is unacceptable.

To avoid this situation the present invention uses once-through regeneration gas, which leads to clean product streams. However, this increases the regeneration gas requirement significantly. The regeneration gas requirement is then reduced by operating the TSA process preferably at lower temperatures. The lower adsorption temperature is chosen such that there is enough regeneration gas produced by the PSA system for once-through 2 bed TSA process. By operating the TSA system at these conditions in a 3 bed mode, net carbon dioxide is produced by the second embodiment of the present invention. This is not achievable in the first embodiment of the present invention.

The extra by-product CO$_2$ generated by the second embodiment CO$_2$/CH$_4$-PSA and not used by the TSA system, is further purified to high grade CO$_2$ by any of the standard techniques, such as liquifaction. This gas stream contains ~3.6% CH$_4$ and ~96.4% CO$_2$. The by-product methane from this CO$_2$ purification section is utilized in part or full as the fuel for TSA thermal combustor. The remaining by product methane is mixed with the primary methane product.

We claim:

1. In the process for purification and recovery of methane from landfill gas by subjecting such gas to pretreatment for removal of trace impurities therefrom followed by bulk separation of CO$_2$ from CH$_4$ from the pretreated gas by selective adsorption, the improvement which comprises; effecting such pretreatment in a multi-column temperature swing adsorption section integrated with a subsequent multi-column pressure swing adsorption section in which the separation of CO$_2$ from CH$_4$ is carried out, wherein a portion of the separated CO$_2$ product recovered from the pressure swing adsorption section is employed in regeneration of adsorbent in the temperature swing adsorption section, wherein the time cycle of adsorption and regeneration in said temperature swing adsorption section is independent of that employed in said pressure swing adsorption section, and wherein the pretreatment of the landfill gas comprises the sequence of steps:

(a) selective adsorption of contained impurities therefrom in an adsorbent bed at super ambient pressure during a predetermined time period while discharging an unadsorbed effluent consisting essentially of CO$_2$ and CH$_4$, (b) thereafter depressuring said bed to ambient pressure level and at said ambient pressure level, (c) thermally regenerating the impurity-laden bed with hot gas obtained by heating a portion of the CO$_2$ product gas from said pressure swing adsorption section, followed by, (d) cooling the bed, and (e) restoring the bed to super-ambient adsorption pressure; and wherein said bulk separation effected in said pressure swing adsorption section comprises at least the sequence of steps:

(1) selective adsorption of CO$_2$ at super-ambient pressure during a predetermined time period while discharging unadsorbed high purity CH$_4$ effluent as a product, (2) depressuring of the column to near-ambient pressure potentially as a $CO_2$ product, followed by, (3) evacuation of said column to sub-atmospheric pressure level thereby removing sorbed $CO_2$ from said column as a $CO_2$ product, and (4) restoring the column to super ambient pressure by introduction therein of part of the $CH_4$ produced in step (1).

2. The improvement as defined in claim 1 wherein step (2) is performed countercurrently.

3. The improvement as defined in claim 1 wherein the $CO_2$ product is a high purity product comprising 98.5% $CO_2$.

4. The improvement as defined in claim 1 wherein step (4) is performed by introducing the $CH_4$ into the column countercurrent to the feed direction.

5. The improvement as defined in claim 1 wherein the total time for carrying out steps (b) through (e) is equal to the cycle time for step (a).

6. The improvement as defined in claim 1 wherein the total cycle time for steps (a) through (e) is in the range of 4 to 16 hours.

7. The improvement as defined in claim 1 wherein the total cycle time for steps 1 to 4 in said pressure swing absorption section is 2 to 60 minutes.

8. The improvement as defined in claim 1 wherein the pressure swing during the cycle in the bulk separation of $CO_2$ from $CH_4$ ranges from sub-atmospheric level at 50–300 torr during evacuation of the column to super ambient pressure in the range of 30–300 psig during the adsorption step.

9. The improvement as defined in claim 1 wherein the thermal regeneration of the impurity-laden adsorbent in step (c) is effected at a temperature in the range of 250° to 900° F.

10. The improvement as defined in claim 1 wherein following (c) regeneration and (d) cooling, the bed is restored to super ambient pressure level by introduction therein of part of the cleaned gas withdrawn from a companion column of the temperature swing adsorption section.

11. The improvement as defined in claim 1 wherein following (c) regeneration and (d) cooling, the bed is restored to super ambient pressure level by introduction therein of part of the $CO_2$ product gas from the pressure swing adsorption section.

12. The improvement as defined in claim 1 wherein the adsorbent for the temperature swing adsorption section beds is activated carbon.

13. In the process for purification and recovery of methane from landfill gas by subjecting such gas to pretreatment for removal of trace impurities therefrom followed by bulk separation of $CO_2$ from $CH_4$ from the pretreated gas by selective adsorption, the improvement which comprises; effecting such pretreatment in a multi-column temperature swing adsorption section integrated with a subsequent multi-column pressure swing adsorption section in which the separation of $CO_2$ from $CH_4$ is carried out, wherein a portion of the separated $CO_2$ product recovered from the pressure swing adsorption section is employed in regeneration of adsorbent in the temperature swing adsorption section, wherein the time cycle of adsorption and regeneration in said temperature swing adsorption section is independent of that employed in said pressure swing adsorption section, and wherein the pretreatment of the landfill gas comprises the sequence of steps:

(a) selective adsorption of contained impurities therefrom in an adsorbent bed at super ambient pressure during a predetermined time period while discharging an unadsorbed effluent consisting essentially of $CO_2$ and $CH_4$, (b) thereafter depressuring said bed to ambient pressure level and at said ambient pressure level, (c) thermally regenerating the impurity-laden bed with hot gas obtained by heating a portion of the $CO_2$ product gas from said pressure swing adsorption section, followed by, (d) cooling the bed, and (e) restoring the bed to super ambient adsorption pressure; and wherein said bulk separation effected in said pressure swing adsorption section comprises the sequence of steps:

(1) selective adsorption of $CO_2$ at super ambient pressure during a predetermined time period while discharging unadsorbed high purity $CH_4$ effluent as a product, (2) co-current rinsing of the $CO_2$/$CH_4$-laden column with $CO_2$ product gas at near feed pressure, (3) countercurrent depressuring of the rinsed column to near ambient pressure, followed by, (4) evacuation of said column to sub-atmospheric pressure level thereby removing sorbed $CO_2$ from said column as a high purity $CO_2$ product, and (5) restoring the column to super ambient pressure by countercurrent introduction therein of part of the $CH_4$ produced in step (1).

14. The improvement as defined in claim 13 wherein the total time for carrying out steps (b) through (e) is equal to the cycle time for step (a).

15. The improvement as defined in claim 13 wherein the total cycle time for steps (a) through (e) is in the range of 4 to 16 hours.

16. The improvement as defined in claim 13 wherein the total cycle time for steps 1 to 5 in said pressure swing adsorption section is 2 to 60 minutes.

17. The improvement as defined in claim 13 wherein the pressure swing during the cycle in the bulk separation of $CO_2$ from $CH_4$ ranges from sub-atmospheric level at 50–300 torr during evacuation of the column to super ambient pressure in the range of 30–300 psig during the adsorption step.

18. The improvement as defined in claim 13 wherein the thermal regeneration of the impurity-laden adsorbent in step (c) is effected at a temperature in the range of 250° to 900° F.

19. The improvement as defined in claim 13 wherein following (c) regeneration and (d) cooling, the bed is restored to super ambient pressure level by introduction therein of part of the cleaned gas withdrawn from a companion column of the temperature swing adsorption section.

20. The improvement as defined in claim 1 wherein following (c) regeneration and (d) cooling, the bed is restored to super ambient pressure level by introduction therein of part of the pure $CO_2$ product gas from the pressure swing adsorption section.

21. The improvement as defined in claim 13 wherein the effluent from the column undergoing rinse of step (2) is recycle to feed to the adsorption of step (1).

22. The improvement as defined in claim 13 wherein the depressurization gas of step (3) is used at least in part to regenerate the bed in step (c).

23. The improvement as defined in claim 13 wherein the effluent from the hot gas regeneration of step (c) is combusted.

24. In the process for purification and recovery of methane from landfill gas by subjecting such gas to pretreatment for removal of trace impurities therefrom followed by bulk separation of $CO_2$ from $CH_4$ from the pretreated gas by selective adsorption, the improvement which comprises; effecting such pretreatment in a multi-column temperature swing adsorption section integrated with a subsequent multi-column pressure swing adsorption section in which the separation of $CO_2$ from $CH_4$ is carried out, wherein at least a portion of the separated methane-containing $CO_2$ product recovered from the pressure swing adsorption section is employed in regeneration of adsorbent in the temperature swing adsorption section, wherein the time cycle of adsorption and regeneration in said temperature swing adsorption section is independent of that employed in said pressure swing adsorption section, and wherein the pretreatment of the landfill gas comprises the sequence of steps:

(a) selective adsorption of contained impurities therefrom in an adsorbent bed at super ambient pressure during a predetermined time period while discharging an unadsorbed effluent consisting essentially of $CO_2$ and $CH_4$, (b) thereafter depressuring said bed to ambient pressure level and at said ambient pressure level, (c) thermally regenerating the impurity-laden bed with hot gas by heating a portion of the methane-containing $CO_2$ product gas from said pressure swing adsorption section, followed by, (d) cooling the bed, and (e) restoring the bed to super ambient adsorption pressure; and wherein said bulk separation effected in said pressure swing adsorption section comprises the sequence of steps:

(1) selective adsorption of $CO_2$ at super ambient pressure during a predetermined time period while discharging unadsorbed high purity $CH_4$ effluent as a product, (2) depressuring of the column to near ambient pressure potentially as a methane-containing $CO_2$ product, followed by, (3) compressing at least a portion of the depressurization gas of step (2) to feed pressure and mixing it with feed to step (1) adsorption, (4) evacuation of said column to sub-atmospheric pressure level thereby removing sorbed $CO_2$ from said column as a methane-containing $CO_2$ product, and (5) restoring the column to super ambient pressure by countercurrent introduction therein of part of the $CH_4$ produced in step (1).

25. The improvement as defined in claim 24 wherein the methane-containing $CO_2$ product gas used to regenerate the TSA column in step (c) is combusted to destroy contained impurities using the methane content of said methane-containing $CO_2$ product gas.

26. The improvement as defined in claim 24 wherein step (2) is performed countercurrent to the adsorption feed direction.

27. The improvement as defined in claim 24 wherein step (2) is performed co-current to the adsorption feed direction.

28. The improvement as defined in claim 24 wherein before step (2) said column is depressurized to a middle pressure level by joining it with the adsorption feed end of a similar column which is finished step (4) evacuation.

29. The improvement as defined in claim 24 wherein step (4) is performed countercurrently to the adsorption feed direction.

30. The improvement as defined in claim 24 wherein step (4) is performed co-currently and countercurrently simultaneously.

31. The improvement as defined in claim 24 wherein prior to step (5) restoration, the feed end of said restoring column is connected to the discharge end of said column undergoing depressurization to a middle pressure.

32. The improvement as defined in claim 24 wherein the total time for carrying out steps (b) through (e) is equal to the cycle time for step (a).

33. The improvement as defined in claim 24 wherein the total cycle time for steps (a) through (e) is in the range of 4 to 16 hours.

34. The improvement as defined in claim 24 wherein the total cycle time for steps 1 to 5 in said pressure swing adsorption section is 2 to 60 minutes.

35. The improvement as defined in claim 24 wherein the pressure swing during the cycle in the bulk separation of $CO_2$ from $CH_4$ ranges from sub-atmospheric level at 50–300 torr during evacuation of the column to super ambient pressure in the range of 30–300 psig during the adsorption step.

36. The improvement as defined in claim 24 wherein the thermal regeneration of the impurity-laden adsorbent in step (c) is effected at a temperature in the range of 250° to 900° F.

37. The improvement as defined in claim 24 wherein following (c) regeneration and (d) cooling, the bed is restored to super ambient pressure level by introduction therein of part of the cleaned gas withdrawn from a companion column of the temperature swing adsorption section.

38. The improvement as defined in claim 24 wherein following (c) regeneration and (d) cooling, the bed is restored to super ambient pressure level by introduction therein of part of the pure $CO_2$ product gas from the pressure swing adsorption section.

* * * * *

UNITED STATES PATENT AND TRADEMARK OFFICE
CERTIFICATE OF CORRECTION

PATENT NO. : 4,770,676
DATED : Sep 13, 1988
INVENTOR(S) : Shivaji Sircar, Ravi Kumar, William R. Koch, John VanSloun It is certified that error appears in the above-identified patent and that said Letters Patent is hereby corrected as shown below:

Column 21, Line 31
    After "gas" insert -- obtained --

Signed and Sealed this

Twenty-third Day of May, 1989

Attest:

DONALD J. QUIGG

Attesting Officer          Commissioner of Patents and Trademarks